United States Patent [19]

Mukaiyama et al.

[11] Patent Number: 4,616,092
[45] Date of Patent: Oct. 7, 1986

[54] β-FORMYL-β-HYDROXY ESTER

[75] Inventors: Teruaki Mukaiyama, Tokyo; Yoji Sakito, Ibaraki; Masatoshi Asami, Yokohama, all of Japan

[73] Assignee: Sumitomo Chemical Company, Limited, Osaka, Japan

[21] Appl. No.: 235,559

[22] Filed: Feb. 18, 1981

[30] Foreign Application Priority Data

Mar. 31, 1980 [JP] Japan ............................... 55-42412

[51] Int. Cl.[4] .......................................... C07C 69/675
[52] U.S. Cl. ............................. 560/177; 260/410.9 R; 549/453; 560/53
[58] Field of Search ................. 560/177, 53; 260/405, 260/410.9 R

[56] References Cited

U.S. PATENT DOCUMENTS 2,857,420 10/1958 Hoffman et al. ..................... 560/177

OTHER PUBLICATIONS

House, Modern Synthetic Reactions, 1972, Menlow Park, CA, pp. 671–673.
Chem. Abstracts, 65:18495c, (1966).
Mukaiyama, Teruaki et al., Chemistry Letters, 705–708 (1979) (Chemical Society of Japan).

*Primary Examiner*—Vivian Garner
*Attorney, Agent, or Firm*—Stevens, Davis, Miller & Mosher

[57] ABSTRACT

An optically active or inactive β-formyl-β-hydroxy ester of the formula (1),

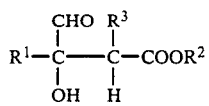 (1)

wherein $R^1$ represents a $C_1$–$C_{10}$ alkyl, $C_3$–$C_{10}$ alkenyl, $C_2$–$C_{10}$ alkynyl, $C_6$–$C_{14}$ aryl or $C_7$–$C_{14}$ aralkyl group, $R^2$ represents a $C_1$–$C_4$ alkyl group and $R^3$ represents a hydrogen atom or a $C_1$–$C_{10}$ alkyl group, and a method for producing the same which comprises reacting an optically active or inactive compound of the formula (2),

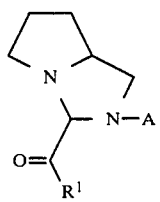 (2)

wherein A represents a $C_6$–$C_{14}$ aryl group and $R^1$ is as defined above, with an α-halo ester of the formula (3),

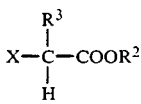 (3)

wherein X represents a halogen atom and $R^2$ and $R^3$ are as defined above, in the presence of zinc, followed by hydrolysis, or reacting an ester of the formula (4),

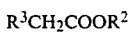 (4)

wherein $R^2$ and $R^3$ are as defined above, with a lithium amide derivative and then with an optically active or inactive compound of the formula (2), followed by hydrolysis.

The compounds of this invention are intermediate materials for production of medicines and agricultural chemicals.

1 Claim, No Drawings

β-FORMYL-β-HYDROXY ESTER

The present invention relates to optically active or inactive β-formyl-β-hydroxy esters and their production.

More particularly, the present invention relates to optically active or inactive β-formyl-β-hydroxy esters of the formula (1),

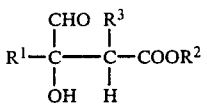
(1)

wherein $R^1$ represents a $C_1$–$C_{10}$ alkenyl, $C_2$–$C_{10}$ alkynyl, $C_6$–$C_{14}$ aryl or $C_7$–$C_{14}$ aralkyl group, $R^2$ represents a $C_1$–$C_4$ alkyl group and $R^3$ represents a hydrogen atom or a $C_1$–$C_{10}$ alkyl group, and a method for producing them. The present invention includes a method which comprises reacting an optically active or inactive compound of the formula (2), 2-acyl-1,3-diazabicyclo-[3.3.0]octane derivatives (referred to as aminal hereinafter),

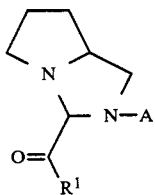
(2)

wherein A represents a $C_6$–$C_{14}$ aryl group and $R^1$ is as defined above, with an α-halo ester of the formula (3),

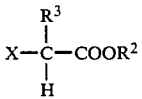
(3)

wherein X represents a halogen atom and $R^2$ and $R^3$ are as defined above, in the presence of zinc, followed by hydrolysis, and a method which comprises reacting an ester of the formula (4),

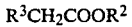  $R^3CH_2COOR^2$ (4)

wherein $R^2$ and $R^3$ are as defined above, with a lithium amide derivative and then with aminal, followed by hydrolysis.

Next, the objective compounds of this invention represented by the formula (1) will be exemplified in $R^1$, $R^2$ and $R^3$.

$R^1$: methyl, ethyl, n-propyl, isopropyl, n-butyl, isobutyl, n-amyl, 2-propenyl, 2-butenyl, 3-butenyl, 2-pentenyl, 3-pentenyl, 4-pentenyl, ethynyl, propargyl, 2-butynyl, 2-pentynyl, 3-pentynyl, phenyl, p-tolyl, benzyl, phenethyl, phenylpropyl group or the like.

$R^2$: methyl, ethyl, n-propyl, isopropyl, n-butyl, isobutyl, tert-butyl group or the like.

$R^3$: hydrogen atom, methyl, ethyl, n-propyl, n-butyl group or the like.

β-Formyl-β-hydroxy esters of the formula (1), the objective compounds of this invention, may become intermediate materials for the production of medicines and agricultural chemicals. Particularly, their optical isomers and production thereof are of an important significance. For example, α-tocopherol [HELV. CHIM. ACTA., 62, 2384 (1979)] derivable from ethyl 3-hydroxy-3-formylbutyrate, one of β-formyl-β-hydroxy ester, wherein $R^1$, $R^2$ and $R^3$ are methyl, ethyl and hydrogen atom respectively in the formula (1), is an important compound known as vitamin E.

Hitherto, β-formyl-β-hydroxy esters of the formula (1) were not known; therefore not only both the optical isomers and racemates are novel compounds but also the process how to prepare them is accomplished for the first time by us.

Aminal of the formula (2) used in the present invention can be produced, as shown in Reference example, using an optically active or inactive 2-(N-substituted aminomethyl)pyrrolidine and glyoxylic acid ester derivative or substituted glyoxal as starting materials.

As examples of a substituent A on the nitrogen of aminal of the formula (2), there may be given for example a phenyl, o-methoxyphenyl, p-methoxyphenyl, 2-pyridyl, 4-pyridyl, 3,4-dichlorophenyl, 1-naphthyl, o-tolyl and 2,6-xylidyl groups.

β-Formyl-β-hydroxy esters, the objective compounds of this invention, can be obtained by carrying out a reaction between aminal and an α-halo ester in the presence of zinc, the so-called Reformatsky reaction, followed by hydrolysis.

As the α-halo ester used in the present invention, the alkyl esters of chloroacetic acid, bromoacetic acid, iodoacetic acid, α-bromopropionic acid, α-bromobutyric acid or the like are given. Specifically, there may be used for example methyl chloroacetate, ethyl chloroacetate, n-propyl chloroacetate, methyl bromoacetate, ethyl bromoacetate, n-propyl bromoacetate, methyl iodoacetate, ethyl iodoacetate, n-propyl iodoacetate, methyl-α-bromopropionate, ethyl-α-bromopropionate, n-propyl-α-bromopropionate, methyl-α-bromobutyrate, ethyl-α-bromobutyrate and n-propyl-α-bromobutyrate. Among these compounds, α-bromo esters are particularly preferred.

As the solvent used for the Reformatsky reaction in this invention, the commonly used ones for this reaction, for example benzene, ether, methylal, tetrahydrofuran and the like, may be used. For producing optically active β-formyl-β-hydroxy esters, however, aromatic hydrocarbons such as benzene and toluene are preferred.

The reaction temperature is not particularly limited. But, for beginning this reaction, heating is necessary in general so that it is desirable to carry out the reaction at the refluxing temperature of the solvent.

Hydrolysis is carried out using an acid such as hydrochloric acid or sulfuric acid. The reaction temperature employed is within a range of −10° C. to 100° C., but lower temperatures are desirable taking into account the stability of β-formyl-β-hydroxy esters.

β-Formyl-β-hydroxy esters, the objective compounds of this invention, can also be produced by allowing an ester of the formula (4) to react with a lithium amide derivative and then with aminal, followed by hydrolysis.

As the ester used in the present invention, alkyl esters are generally used. Specifically, there may be used, for example, methyl acetate, ethyl acetate, n-propyl acetate, isopropyl acetate, methyl propionate, ethyl propionate, n-propyl propionate, isopropyl propionate, methyl butyrate, ethyl butyrate, n-propyl butyrate and isopropyl butyrate.

The lithium amide derivative used in this invention includes for example lithium diisopropylamide, lithium dicyclohexylamide, lithium N-isopropylcyclohexylamide, lithium 2,2,6,6-tetramethylpiperizide and lithium bistrimethylsilylamide.

The solvent used in this reaction includes for example ether, tetrahydrofuran, toluene and methylal.

For this reaction, a lower reaction temperature is desirable, for example, reaction temperatures lower than 0° C., preferably less than −20° C., more preferably less than −50° C., are advantageous. Hydrolysis may be carried out in the same manner as described hereinbefore.

The present invention will be illustrated specifically with reference to the following examples, which are not however to be interpreted as limiting the invention thereto.

EXAMPLE 1

5-(S)-2-Benzoyl-3-phenyl-1,3-diazabicyclo-[3.3.0]octane (572 mg) was dissolved in benzene (30 ml), and zinc powder (197 mg) and ethyl bromoacetate (491 mg) were added thereto. The mixture was then heated under reflux for 1 hour. After cooling to room temperature, an ammonium chloride-saturated aqueous solution (20 ml) was added to wash the organic layer. To the organic layer was added 2% hydrochloric acid (25 ml), followed by 2 hours' stirring at room temperature. The organic layer was separated, and the aqueous layer was extracted with ether. The ether extract and the organic layer were combined and washed with sodium chloride-saturated water. The solvent was then removed under reduced pressure, and the residue obtained was purified by column chromatography on silica gel to obtain 251 mg of ethyl β-formyl-β-hydroxy-β-phenylpropionate.

NMR peak δ(ppm): 1.18(3H, triplet), 2.79(1H, doublet), 3.27(1H, doublet), 4.04(2H, quartet), 4.83(1H, singlet), 7.20(5H, multiplet), 9.32(1H, singlet).

$[\alpha]_D^{24} = -135°$ (c=2.53, benzene), the optical yield is 88%.

The optical yield was determined by changing the product to 2,2-dimethyl-4-phenyl-4-(2-hydroxyethyl)-1,3-dioxolan, measuring the NMR spectrum of the compound with addition of an optically active shift reagent and calculating the ratio of two peak areas obtained by integration.

EXAMPLE 2

Lithium diisopropylamide was prepared from diisopropylamine (520 mg) in tetrahydrofuran and n-butyllithium (5.15 mmole) (0.64 ml/mmole of n-hexane solution).

After cooling to −78° C., a solution of ethyl acetate (476 mg) in tetrahydrofuran was added dropwise thereto, followed by stirring for 30 minutes. Further, a solution of 5-(S)-2-benzoyl-3-phenyl-1,3-diazabicyclo[3.3.0]octane (928 mg) in tetrahydrofuran was added dropwise at −78° C., followed by reaction for 1 hour. The reaction was stopped with addition of 2% hydrochloric acid (50 ml). The reaction solution was then raised to room temperature, and after adding ether (20 ml), it was stirred at room temperature for 2 hours. The organic layer was separated, and isolation and purification of the product were carried out in the same manner as in Example 1 to obtain 597 mg of ethyl β-formyl-β-hydroxy-β-phenylpropionate.

$[\alpha]_D^{26} = +96.3°$ (c=3.16, benzene), the optical yield is 62%.

EXAMPLE 3

Lithium diisopropylamide was prepared from diisopropylamine (341 mg) in toluene and n-butyllithium (3.4 mmole) (0.641 ml/mmole of n-hexane solution). After cooling to −78° C., a solution of ethyl acetate (548 mg) in toluene was added dropwise thereto, followed by stirring for 30 minutes.

Further, a solution of 5-(S)-2-benzoyl-3-(o-methoxyphenyl)-1,3-diazabicyclo[3.3.0]octane (548 mg) in toluene was added dropwise at −78° C., followed by reaction for 1 hour. The reaction was stopped with addition of 2% hydrochloric acid (40 ml). The reaction solution was then raised to room temperature, and after adding ether (20 ml), it was stirred at room temperature for 2 hours. The organic layer was separated, and isolation of the product was carried out in the same manner as in Example 1 to obtain 324 mg of ethyl β-formyl-β-hydroxy-β-phenylpropionate.

$[\alpha]_D^{26} = -128°$ (c=1.92, benzene), which means that the optical yield is 84%.

EXAMPLE 4

Procedure was carried out in the same manner as in Example 3 except that 5-(S)-2-acetyl-3-(o-methoxyphenyl)-1,3-diazabicyclo[3.3.0]octane (443 mg) was used in place of 5-(S)-2-benzoyl-3-(o-methoxyphenyl)-1,3-diazabicyclo[3.3.0]octane. Thus, 191 mg of ethyl β-formyl-β-hydroxybutyrate was obtained.

NMR peak δ(ppm): 1.20(3H, single), 1.20(1H, triplet), 2.43(1H, doublet), 2.80(1H, doublet), 4.03(2H, quartet), 4.06(1H, singlet), 9.42(1H, singlet).

$[\alpha]_D^{23} = -26.2°$ (c=2.20, benzene), the optical yield is 92%.

The optical yield was determined by changing the product to 2,2,4-trimethyl-4-(2-hydroxyethyl)-1,3-dioxolan, measuring the NMR spectrum of the compound with addition of an optically active shift reagent and calculating the ratio of the two peak areas obtained by integration.

EXAMPLE 5

Procedure was carried out in the same manner as in Example 3 except that 5-(S)-2-propionyl-3-(o-methoxyphenyl)-1,3-diazabicyclo[3.3.0]octane (466 mg) was used in place of 5-(S)-2-benzoyl-3-(o-methoxyphenyl)-1,3-diazabicyclo[3.3.0]octane. Thus, 190 mg of ethyl β-formyl-β-hydroxyvalerate was obtained.

NMR peak δ(ppm): 0.87(3H, triplet), 1.23(3H, triplet), 1.38-1.75(2H, multiplet), 2.40(1H, doublet), 2.73(1H, doublet), 3.86(1H, broad), 4.03(2H, quartet), 9.50(1H, singlet).

$[\alpha]_D^{24} = -17.5°$ (c=4.20, benzene), the optical yield is 87%.

The optical yield was determined by changing the product to 2,2-dimethyl-4-ethyl-4-(2-hydroxyethyl)-1,3-dioxolan, measuring the NMR spectrum of the compound with addition of an optically active shift reagent and calculating the ratio of the two peak areas obtained by integration.

EXAMPLE 6

Procedure was carried out in the same manner as in Example 3 except that 5-(S)-2-isobutylyl-3-(o-methoxyphenyl)-1,3-diazabicyclo[3.3.0]octane (490 mg) was used in place of 5-(S)-2-benzoyl-3-(o-methoxyphenyl)-

1,3-diazabicyclo[3.3.0]octane. Thus, 160 mg of ethyl β-formyl-β-hydroxy-γ-methylvalerate was obtained.

NMR peak δ(ppm): 0.88(3H, doublet), 0.91(3H, doublet), 1.23(3H, triplet), 1.53–2.08(1H, multiplet), 2.41(1H, doublet), 2.78(1H, doublet), 4.00(1H, singlet), 4.03(2H, quartet), 9.41(1H, singlet).

$[\alpha]_D^{23} = -25.6°$ (c=4.16 benzene), the optical yield is 92%.

The optical yield was determined by changing the product to 2,2-dimethyl-4-isopropyl-4-(2-hydroxyethyl)-1,3-dioxolan, measuring the NMR spectrum of the compound with addition of an optically active shift reagent and calculating the ratio of the two peak areas obtained by integration.

REFERENCE EXAMPLE 1

(S)-2-(o-Anisidinomethyl)pyrrolidine (72 mg) was allowed to react with phenylglyoxal hydrate (53 mg) for 30 minutes while removing water azeotropically under benzene refluxing. The reaction product was purified by column chromatography on alumina to obtain 101 mg of 5-(S)-2-benzoyl-3-(o-methoxyphenyl)-1,3-diazabicyclo[3.3.0]octane.

REFERENCE EXAMPLE 2

(S)-2-(o-Anisidinomethyl)pyrrolidine (206 mg) was allowed to react with methyl hydroxymethoxyacetate (120 mg) for 30 minutes while removing water azeotropically under benzene refluxing. The solvent was then removed under reduced pressure, and the residue obtained was dissolved in tetrahydrofuran. After adding anhydrous magnesium chloride (210 mg) thereto, the solution was heated under reflux for 1 hour.

After cooling to −78° C., a solution of isopropylmagnesium in ether was added dropwise thereto until disappearance of the starting material was confirmed by thin layer chromatography. Thereafter, an ammonium chloride-saturated aqueous solution was added, and the reaction solution was raised to room temperature, followed by extraction with ether. The ether layer was washed with sodium chloride-saturated water, and the solvent was removed under reduced pressure. The crude product obtained was purified by column chromatography on alumina to obtain 193 mg of 5-(S)-2-isobutylyl-3-(o-methoxyphenyl)-1,3-diazabicyclo[3.3.0]octane.

What is claimed is:

1. An optically active or inactive ethyl β-formyl-β-hydroxybutyrate.

* * * * *